US 6,533,987 B2

(12) United States Patent
Topolkaraev et al.

(10) Patent No.: US 6,533,987 B2
(45) Date of Patent: *Mar. 18, 2003

(54) METHODS OF MAKING MATERIALS HAVING SHAPE-MEMORY

(75) Inventors: Vasily A. Topolkaraev, Appleton, WI (US); Thomas Walter Odorzynski, Green Bay, WI (US); Dave Allen Soerens, Neenah, WI (US); Michael J. Garvey, Appleton, WI (US); Duane Girard Uitenbroek, Little Chute, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 173 days.

This patent is subject to a terminal disclaimer.

(21) Appl. No.: 09/738,549

(22) Filed: Dec. 15, 2000

(65) Prior Publication Data
US 2002/0135103 A1 Sep. 26, 2002

(51) Int. Cl.[7] .............. B06B 1/02; B29C 55/04; B29C 55/10; H05B 6/00; H05B 6/64
(52) U.S. Cl. .............. 264/442; 264/288.4; 264/290.2; 264/479; 264/488; 264/489
(58) Field of Search .............. 264/288.4, 290.2, 264/422, 479, 488, 489, 495

(56) References Cited

U.S. PATENT DOCUMENTS

| RE22,038 E | 2/1942 | Milas |
|---|---|---|
| 2,509,674 A | 5/1950 | Cohen |
| 3,560,292 A | 2/1971 | Butter |
| 3,616,770 A | 11/1971 | Blyther et al. |
| 3,819,401 A | 6/1974 | Massengale et al. |
| 3,860,003 A | 1/1975 | Buell |
| 3,912,565 A | 10/1975 | Koch et al. |
| RE28,688 E | 1/1976 | Cook |
| 4,239,578 A | 12/1980 | Gore |
| 4,261,782 A | 4/1981 | Teed |
| 4,309,236 A | 1/1982 | Teed |
| 4,324,245 A | 4/1982 | Mesek et al. |
| 4,352,355 A | 10/1982 | Mesek et al. |
| 4,675,139 A | 6/1987 | Kehe et al. |
| 4,681,580 A | 7/1987 | Reising et al. |
| 4,710,189 A | 12/1987 | Lash |
| 4,820,590 A | 4/1989 | Hodgson, Jr. et al. |
| 5,429,856 A | 7/1995 | Krueger et al. |
| 5,536,921 A | 7/1996 | Hedrick et al. |
| 5,916,203 A | 6/1999 | Brandon et al. |
| 5,950,325 A | 9/1999 | Mehdizadeh et al. |
| 6,419,798 B1 * | 7/2002 | Topolkaraev et al. .. 204/157.15 |

FOREIGN PATENT DOCUMENTS

GB 2 160 473 A 5/1985

* cited by examiner

Primary Examiner—Leo B. Tentoni
(74) Attorney, Agent, or Firm—Kilpatrick Stockton LLP

(57) ABSTRACT

The present invention relates to shape deformable materials, which are capable of (1) being deformed, (2) storing an amount of shape deformation, and (3) recovering at least a portion of the shape deformation when exposed to electromagnetic radiation (EMR) energy. The shape deformable materials can advantageously be in the form of films, fibers, filaments, strands, nonwovens, and pre-molded elements. The shape deformable materials of the present invention may be used to form products, which are both disposable and reusable. More specifically, the shape deformable materials of the present invention may be used to produce products such as disposable diapers, training pants, incontinence products, and feminine care products.

22 Claims, 5 Drawing Sheets

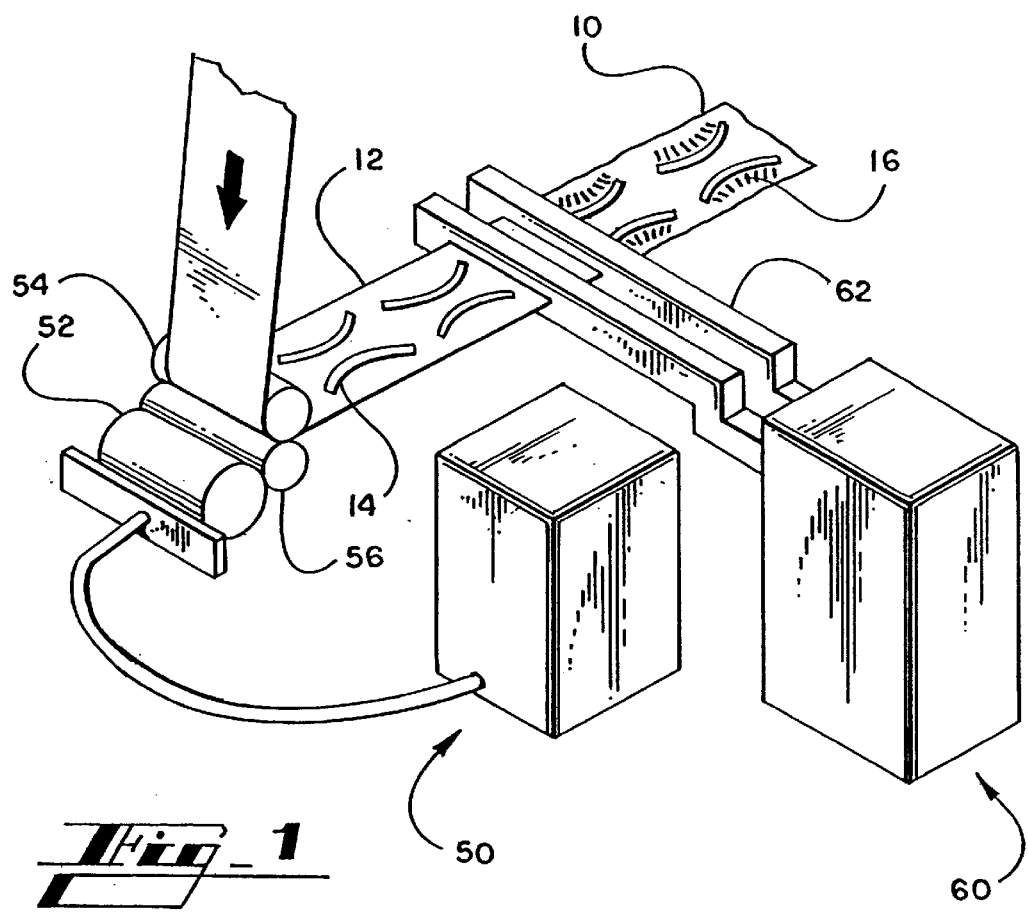
Fig_1
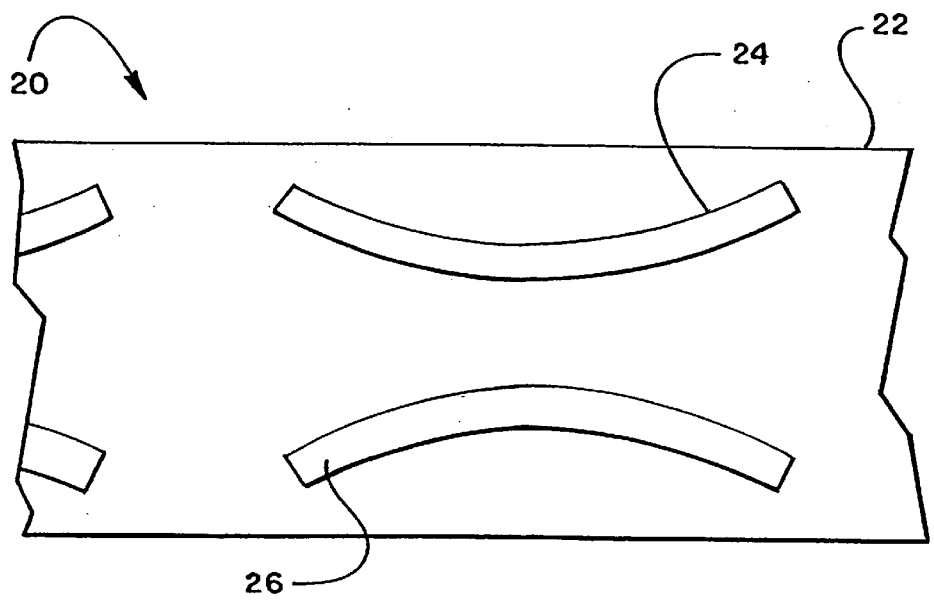
Fig_2

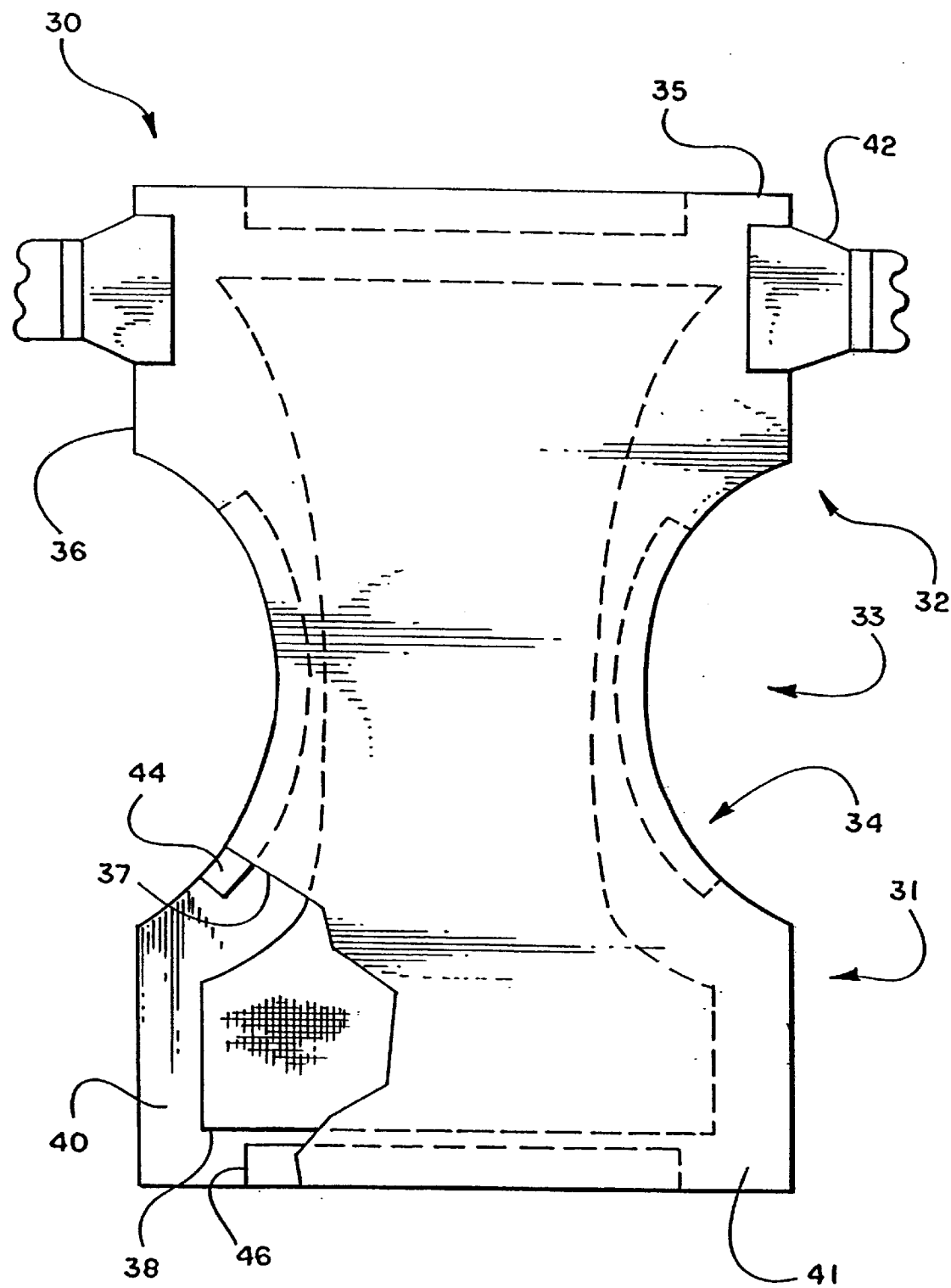
Fig_3

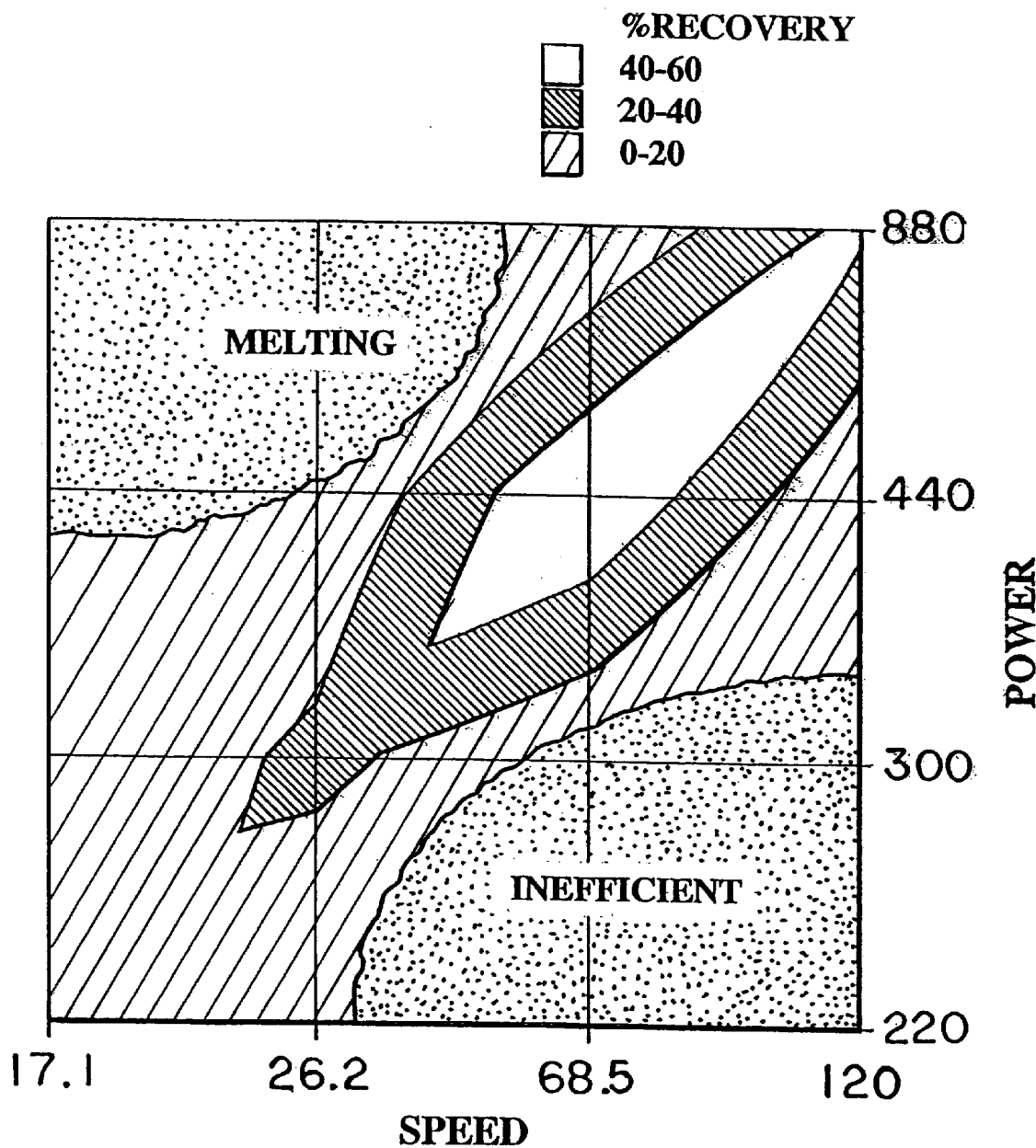
DETERMINING OPTIMUM POWER AND SPEED
OF INDUSTRIAL MICROWAVE UNIT
Fig_4

METHODS OF MAKING MATERIALS HAVING SHAPE-MEMORY

FIELD OF THE INVENTION

The present invention relates to a method of causing the shape deformation of a material by subjecting the material to electromagnetic radiation.

BACKGROUND OF THE INVENTION

Elastomeric materials have been long and extensively used in garments, both disposable and reusable products. These elastomeric materials may be attached to the disposable product by several methods. At one time, elastic was applied to the substrate by sewing. (See U.S. Pat. No. 3,616,770 to Blyther et al.; and U.S. Pat. No. 2,509,674 and RE 22,038 to Cohen). A newer method for attaching elastomeric material to a substrate is by use of an adhesive. (See U.S. Pat. No. 3,860,003 to Buell.) Welding, such as sonic welding, has also been used to attach elastomeric material to a disposable product. (U.S. Pat. No. 3,560,292 to Butter). Laminates having an elastomeric layer and a co-extensive skin layer have also been used. (U.S. Pat. No. 5,429,856 to Kruger et al.).

These methods of attachment present several problems. First is the problem of how to keep the elastic in a stretched condition while applying the elastic to the substrate. Another problem is that attachment of a ribbon of elastomeric material will concentrate the elastomeric force in a relatively narrow line. This may cause the elastic to pinch and irritate the wearer's skin. (See U.S. Pat. Nos. 3,860,003; 4,352,355; and 4,324,245 to Musek et al.; U.S. Pat. No. 4,239,578 to Gore; and U.S. Pat. Nos. 4,309,236 and 4,261,782 to Teed.) Other disadvantages of conventional attachment methods include speed, ease of manufacture, and cost. More importantly, difficulties may be encountered in maintaining a uniform tension on the elastic layer during its attachment to the substrate and also in handling the shirred article once the elastic layer is relaxed.

Heat-responsive elastomeric films overcome some of these detriments. Heat-responsive elastomers exist in two forms: a thermally-stable and a thermally-unstable form. The thermally-unstable form is created by stretching the material while heating near its crystalline or second phase transition temperature, followed by a rapid quenching to freeze in the thermally-unstable, extended form. The elastomeric film can then be applied to a disposable product, for example a diaper, and heated to shirr or gather the elastomeric material, thereby producing a thermally-stable, stable form of the elastomeric material. Examples of heat-responsive elastomeric films are disclosed in U.S. Pat. No. 4,681,580 to Reising et al., U.S. Pat. No. 4,710,189 to Lash, U.S. Pat. No. 3,819,401 to Massengale et al., U.S. Pat. No. 3,912,565 to Koch et al., and U.S. Pat. No. RE 28,688 to Cook.

These polymers have several disadvantages. The first of these disadvantages involves the temperature to which the elastomeric material must be heated to stretch the material to its thermally-unstable form. This temperature is an inherent property of the elastomeric material. Therefore, the disposable product is often difficult to engineer because temperatures useful for the production of the overall product may not be compatible with the temperature necessary to release the thermally-unstable form of the elastomer. Frequently, this temperature is rather high and can be detrimental to the adhesive material used to attach the various product layers.

Another drawback to the use of heat-responsive elastomers is that they can constrain the manufacturing process, rendering it inflexible to lot variations, market availability, cost of raw materials, and customer demands.

U.S. Pat. No. 4,820,590 to Hodgkin et al. describes an elastomeric blend of three components to reduce the temperature required for the material to resume its heat stable form. Additionally, GB Patent 2,160,473 to Matray et al. proposes an elastomer which will shrink at an elevated temperature, for example at or above 170° F. The advantageous features of these materials, compared to the heat-shrinkable materials discussed above, is that it does not require preheating during the stretching operation, but rather can be stretched at ambient temperatures by a differential speed roll process or by "cold rolling."

Problems with use of these elastomers include difficulties inherent in applying a stretched elastic member to a flexible substrate such as a disposable diaper. Although some of the elastomers proposed have the advantage that they can be applied at ambient conditions in a highly stretched, unstable form, subsequent, often extreme, heating is required to release the thermally-unstable form to a contracted thermally-stable form. The temperature of this heat release is generally inflexible since it is determined at the molecular level of the elastomer. Thus, selection of materials for the disposable product which are compatible with this heating step is required.

Further, when individual heat activated elastic materials are used, the heat activation is generally accomplished by passing the garments through a heated air duct for a period of time. Since thermal heating must be transferred from an outer surface of the garment to inner portions of the garment, distribution of the activation means (i.e., thermal heat) throughout the garment takes considerable amounts of time and energy, resulting in an inefficient activation process. In such a configuration, the activation process typically takes several seconds, or even minutes, to elevate the temperature of the elastic material to a level at which activation takes place, causing the elastic material to retract and gather the garment. As a result, such heating processes can consume vast amounts of energy and undesirably result in slower manufacturing speeds.

What is needed in the art is a method of activating a shape deformation of a material within 1 second and without using an inefficient thermal heating activation process. What is also needed in the art is a method of activating a shape deformation of a material without substantially increasing the temperature of the material.

SUMMARY OF THE INVENTION

The present invention addresses some of the difficulties and problems discussed above by the discovery of materials capable of exhibiting a shape deformation when exposed to electromagnetic radiation. These materials exhibit a change in at least one spatial dimension when subjected to an activation energy for less than one second. The materials of the present invention find applicability in a number of products, including products containing a gatherable or elastic part.

The present invention is further directed to a method of causing the shape deformation of materials having a desired amount of locked-in shape deformation. The method comprises subjecting the material to an activation energy for an amount of time, typically less than about one second. The method may be used to cause the shape deformation of the above-described material itself or a product containing the above-described material.

In addition, the present invention is directed to articles of manufacture, which contain the above-described materials having a desired amount of locked-in shape deformation. Suitable products include, but are not limited to, products containing an elastic portion, such as diapers, as well as, products having a shrinkable or expandable component. The present invention is also directed to a method of making various articles of manufacture, which contain the above-described materials having a desired amount of locked-in shape deformation, and are subsequently subjected to electromagnetic energy.

The present invention is also directed to a method of building shape deformable polymers in an effort to optimize the interaction of the shape deformable polymer with a selected activation energy. By adjusting the chemical structure of the shape deformable polymer, one can tailor a specific shape deformable polymer in such a way as to maximize the interaction of the shape deformable polymer with a selected activation energy, such as electromagnetic energy (EMR) having a specific wavelength.

These and other features and advantages of the present invention will become apparent after a review of the following detailed description of the disclosed embodiments and the appended claims.

BRIEF DESCRIPTION OF THE DRAWINGS

The present invention is further described by the accompanying drawings, in which:

FIG. 1 representatively shows a perspective view of a method according to one embodiment of the present invention;

FIG. 2 representatively shows a top plan view of a composite material according to one embodiment of the present invention;

FIG. 3 representatively shows a partially cut away, top plan view of an absorbent article according to one embodiment of the present invention; and FIG. 4 graphically shows the optimum percent recovery range for a specific shape deformation material and its relationship to the combined effects of power of an industrial microwave generator and the speed of the shape deformation material through the industrial microwave generator.

DETAILED DESCRIPTION OF THE INVENTION

Figure 5:
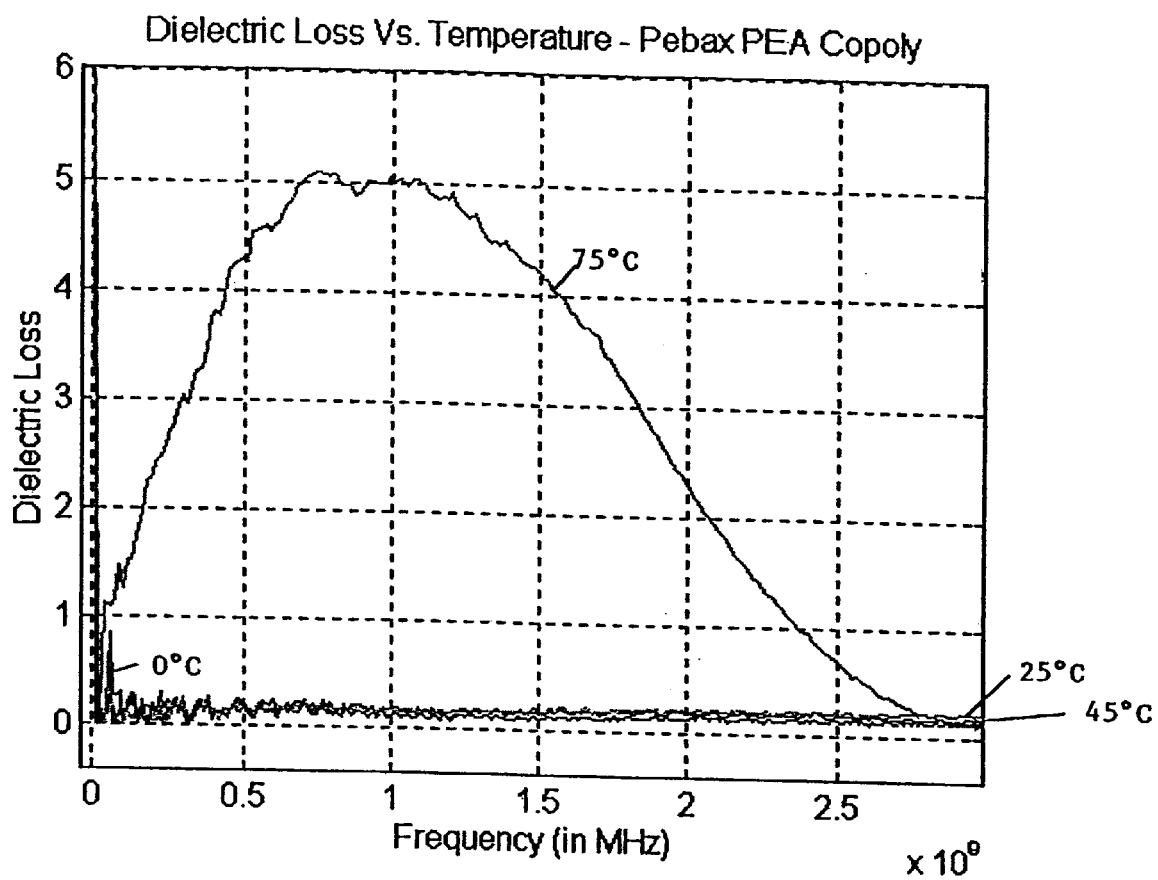
FIG. 5 graphically displays the change in value of the dielectric loss factor of polyether amide versus frequency at selected temperatures.

The present invention addresses some of the difficulties and problems discussed above by the discovery of materials, which are capable of exhibiting a shape deformation when exposed to electromagnetic radiation (EMR), and methods of using the same. These materials exhibit a change in at least one spatial dimension when subjected to an activation energy for less than about one second. Unlike known materials and methods, the materials and methods of the present invention maximize the amount of "locked-in" shape deformation within the material, as well as, maximize the percent change in one or more spatial dimensions of the material. Further, unlike previous recovery methods which involve a heating step, the present invention is directed to a method of causing a change in one or more spatial dimensions of the material without a substantial change in the temperature of the material. The recovery method of the present invention instead comprises subjecting the material to an amount of electromagnetic radiation sufficient to cause a desired change in one or more spatial dimensions without a substantial change in the temperature of the material. The materials and methods of the present invention find applicability in a number of products and processes.

One method of measuring the change in one or more spatial dimensions of a material is given by the equation below:

$$\% R = \frac{(\delta_i - \delta_f)}{\delta_i} \times 100$$

wherein:

%R represents the percent change, or the percent recovery, of one spatial dimension of the material;

$\delta_i$ represents the dimension prior to subjection to an activation energy; and $\delta_f$ represents the dimension after subjection to the activation energy.

The above equation may be used to determine the percent recovery of one or more spatial dimensions of the shape deformable material of the present invention. Further, the above equation may be used on any material capable of experiencing a change in a spatial dimension. Suitable materials having a shape deformation and a desired percent recovery are given below.

Shape Deformable Material Components

The present invention is directed to shape deformable materials, which exhibit a change in at least one spatial dimension when subjected to an activation energy of electromagnetic radiation for less than about one second. Suitable materials include any material or blend of materials, which has the following properties: (1) is capable of being deformed in at least one spatial dimension when exposed to one or more external forces, (2) is capable of maintaining a degree of deformation in at least one spatial dimension once the external force is removed, and (3) is capable of exhibiting a change, or percent recovery, in at least one spatial dimension when subjected to an activation energy in the form of electromagnetic radiation for less than about one second. The shape deformable materials of the present invention may contain one or more of the following classes of components:

Shape Deformable Matrix Materials

The shape deformable materials of the present invention contain at least one shape deformable matrix material. As used herein, the term "shape deformable matrix material" is used to describe a material having the three above-mentioned properties, and is also capable of encompassing one or more filler materials. Suitable shape deformable matrix materials include, but are not limited to, polymers and ionomer resins. Examples of ionomer resins useful in the present invention include, but are not limited to, polyurethane ionomer resins and segmented block copolymer ionomer resins. Other ionomer resins, e.g. ionomer resins known under the trade name SURLYN® (available from DuPont) may also be used. Preferably, the ionomer resins used have a high ion content.

In one embodiment of the present invention, the shape deformable matrix material comprises at least one polymer having the above-mentioned properties. Suitable polymers include, but are not limited to, segmented block copolymers comprising one or more hard segments and one or more soft segments; polyester-based thermoplastic polyurethanes; polyether-based polyurethanes; polyethylene oxide; polybutylene succinate; polybutylene succinate-adipate; polyhydroxybutyrate-co-valerate; polycaprolactone; poly (ether ester) block copolymers; sulfonated polyethylene terephthalates; poly(vinylidene chloride); vinylidene chloride-containing copolymers; polylactides; polyamides; poly(amide esters); poly(ether amide) copolymers; and mixtures thereof. Desirably, the shape deformable matrix material comprises a segmented block copolymer comprising one or more hard segments and one or more soft segments, where either the soft segment, the hard segment, or both contain functional groups or receptor sites that are responsive to electromagnetic radiation (EMR).

As used herein, the phrase "responsive to electromagnetic radiation (EMR)" is used to describe functional groups and/or receptor sites within a polymer, which, when exposed to electromagnetic radiation, convert the electromagnetic radiation into molecular rotational energy, which enables a desired amount of shape recovery of a shape deformed polymer. Suitable functional groups and/or receptor sites include, but are not limited to, functional groups such as urea, sulfone, amide, nitro, nitrile, isocyanate, ketone, ester, aldehyde, phenol, carboxyl, vinylidene chloride, ethylene oxide, methylene oxide, epoxy, and amine groups; ionic groups, such as sodium, zinc, and potassium; and receptor sites having an unbalanced charge distribution formed from one or more of the above groups. Desirably, the functional groups comprise one or more functional groups having a high dipole moment (i.e., greater than about 1.5 Debye) such as urea, sulfone, amide, nitro, nitrile, isocyanate, and ketone groups.

More desirably, the segmented block copolymer is an elastomer. Suitable shape deformable elastomers for use in the present invention include, but are not limited to, polyurethane elastomers, polyether elastomers, poly(ether amide) elastomers, polyether polyester elastomers, polyamide-based elastomers, and mixtures of these polymers. Some non-elastomeric polymers may be used. These polymers can provide some degree of recovery when exposed to activation energy such as heat or EMR. Examples of non-elastomeric polymers useful in the present invention include, but are not limited to, polybutylene succinate, polybutylene succinate-adipate copolyesters, polyethylene oxide, polymers of polylactic acid, blends and mixtures thereof.

In one embodiment of the present invention, the shape deformable matrix material comprises a polyurethane. Suitable polyurethanes for use in the present invention include, but are not limited to, polyester-based aromatic polyurethanes, polyester-based aliphatic polyurethanes, polyether-based aliphatic and aromatic polyurethanes, polyurea, and blends and mixtures of these polyurethanes. Such polyurethanes may be obtained, for example, from Morton International (Chicago, Ill.). Examples of specific polyurethanes, which can be used in the present invention include, but are not limited to, MORTHANE® PS 370-200, MORTHANE® PS 79-200, MORTHANE® PN3429, and MORTHANE ® PE 90-100.

In a further embodiment of the present invention, the shape deformable matrix material includes a poly(ether amide) elastomer. Poly(ether amide) elastomers, which may be used in the present invention, may be obtained, for example, from Elf Atochem North America, Inc. (Philadelphia, Pa.). Examples of such poly(ether amide) elastomers include, but are not limited to, PEBAX® 2533, PEBAX® 3533, and PEBAX® 4033.

Polyurethane elastomers and poly(ether amide) elastomers are particularly useful as the shape deformable matrix material in the present invention because they structurally consist of soft and hard segments, which contain groups having high dipole moments (i.e., isocyanate, amide, and ester groups), which, as discussed above, are highly receptive to electromagnetic radiation. The hard segments in these elastomers typically act as physical cross-linking points for the soft segments, enabling an elastomeric performance. Both hard and soft segments may contribute to the shape deformation during a number of pre-activation treatments described below, such as stretching, which provides "locked-in" shape deformation, which may be recoverable by exposure to an amount of activation energy in the form of EMR for less than about one second.

In still another embodiment of the present invention, the shape deformable matrix material includes a blend of an elastomeric polymer and a non-elastomeric polymer. These blends may either be co-extruded together, or may be formed into multi- or micro-layer structures. These blends are advantageous since blending or multi-layering/microlayering of a shape deformation elastomer with another non-elastomeric shape deformation polymer can improve latent deformation properties, especially at lower stretching temperatures, and can significantly increase recoverable deformation as a result of activation by thermal energy or EMR energy.

EMR Absorbers

Desirably, the shape deformable material of the present invention further comprises one or more electromagnetic radiation (EMR) absorbers. As used herein, the term "EMR absorber" is used to describe additives, which further enhance the conversion of EMR energy into molecular rotational energy of the shape deformable material, which results in enhanced relaxation of the molecular structure of the shape deformable matrix material (i.e., ability to recovery from a latent, locked-in state). Examples of suitable EMR absorbers for use in the shape deformable materials of the present invention include, but are not limited to, silicon oxide, aluminum oxide, aluminum hydroxide, carbon black, zinc oxide, barium titanate, and mixtures of these. Other suitable EMR absorbers include organic polymeric absorbers such as electrically conductive polymers, e.g., polyanilines, polypyrroles and polyalkythiophenes, and chiral polymers. EMR absorption of electrically conductive polymers may be improved through doping. Chiral compounds useful as EMR absorbers are characterized as being optically active, which means they can rotate the plain optical polarization in certain isotropic media, and they are not superimposable on its mirror image.

EMR absorbers may be present within the shape deformable matrix material or may be on one or more surfaces of the shape deformable matrix material. Further, the EMR absorbers may be uniformly distributed within the shape deformable matrix material or may be non-uniformly distributed within the shape deformable matrix material. In the latter case, a shape deformable material may be produced, which exhibits non-uniform recovery of a latent, locked-in deformation when exposed to an activation energy.

It should be noted that one or more of the above-mentioned EMR absorbers may be used in combination with one or more shape deformable matrix materials to prepare the shape deformation materials of the present invention. Further, it should be noted that one or more of the above-mentioned shape deformable polymers, alone or in combination with one or more of the above-mentioned EMR absorbers, may be used in combination with one or more non-activatable materials to form a blend of shape deformable material.

Non-Activatable Materials

As used herein, the term "non-activatable materials" is used to describe any material, which lacks one or more of the three properties mentioned above when describing suitable shape deformable materials. Suitable non-activatable additional materials include, but are not limited to, non-elastomeric polymers, tackifiers, anti-blocking agents, fillers, antioxidants, UV stabilizers, polyolefin-based polymers and other cost-saving additives that may be added or blended to add beneficial properties.

The amount of non-activatable material blended with the above-mentioned shape deformable polymers and EMR absorbers may vary as long as the resulting blend possesses a desired amount of shape deformation properties. The blend may contain from about 40 to 99.5 weight percent of shape deformable polymer/EMR absorbers and from about 60 to 0.5 weight percent of additional non-activatable materials. Desirably, the blend contains from about 60 to 99.5 weight percent of shape deformable polymer/EMR absorbers and from about 40 to 0.5 weight percent of additional materials. More desirably, the blend contains from about 80 to 99.5 weight percent of shape deformable polymer/EMR absorbers and from about 20 to 0.5 weight percent of additional non-activatable materials.

Configuration of Shape Deformable Materials

The shape deformation materials of the present invention may possess a variety of shapes and sizes. The shape deformation materials of the present invention may be in the form of films, multi-layered or micro-layered films, laminates, filaments, fabrics, foams, or any other three-dimensional form. The shape deformation material may be formed by any method known to those of ordinary skill in the art including, but not limited to, extrusion, spray coating, foaming, etc. There is no limitation on the size of the shape deformation material; however, the amount of shape deformation and the percent recovery of the shape deformation material may be limited if the size of the material is too great.

In an alternative embodiment, materials that include a blend of two shape-deformable polymers or a multi- or micro-layer structure having two shape-deformable polymers demonstrate that blending or multi-layering/micro-layering of a shape deformation elastomer with another non-elastomeric shape deformation polymer can improve latent deformation properties, especially at lower stretching temperatures, and can significantly increase recoverable deformation as a result of activation by thermal energy or EMR energy.

Regardless of the size and shape of the shape deformation material, the shape deformation material of the present invention exhibits a change in at least one spatial dimension when subjected to an activation energy for less than about one second. Typically, the shape deformation material of the present invention exhibits a change in one, two, or three dimensions. For example, when the shape deformation material is in the form of a fiber, the shape deformation material exhibits a change in the fiber length and/or fiber diameter. When the shape deformation material is in the form of a film, the shape deformation material exhibits a change in the film length and/or film width and film thickness. A percent recovery may be measured for each of the dimensions of the shape deformation material.

As can be seen by the above equation, in order to maximize the percent recovery of a given dimension, %R, the difference between the dimension prior to ($\delta_i$) and after subjection to an activation energy ($\delta_f$) needs to be maximized. The present invention provides a method of maximizing the percent recovery, %R, of a given dimension of a material. One factor, which effects the ability to maximize the present recovery of a given dimension, is the ability to "lock-in" a desired amount of shape deformation in the material prior to subjecting the material to an activation energy.

Preparation of Materials Having a Degree of Shape Deformation

One aspect of the present invention is directed to a method of preparing materials having a desired amount of "locked-in" shape deformation. As used herein, the term "locked-in shape deformation" refers to a recoverable amount of shape deformation in one or more spacial dimensions of a given material, resulting from one or more forces exerted on the given material. Suitable forces include, but are not limited to, stretching, heating, cooling, compressing, etc. The amount of locked-in shape deformation may vary depending upon a number of factors including, but not limited to, the material composition, the material temperature, the material treatment procedures (i.e., the amount of stress administered to the material), and any post-treatment procedures (i.e., quenching, tension, etc.). A number of factors, which may contribute to the locked-in shape deformation of a given material are discussed below.

Stretching or Compressing

Stretching and compressing are ways to impart a locked-in shape deformation to a shape deformation material of the present invention. The amount of deformation resulting from stretching or compressing is dependent upon a number of variables. Important variables associated with stretching or compressing of a given material include, but are not limited to, the stretch or draw ratio, the stretching or compressing temperature, the stretching or compressing rate, and post-stretching or post-compressing operations, if any, such as heat setting or annealing operations.

Additionally, other types of deformation may be used besides stretching and compressing including, but not limited to, bending, twisting, shearing, or otherwise shaping the material using complex deformations.

Stretch or Draw Ratio

The amount of locked-in shape deformation that can be imparted to a given material depends upon the stretch or draw ratio. In general, the amount of locked-in shape deformation of a material is typically larger when the draw ratio is larger. Stretching of the material may be accomplished in one or more directions, such as uniaxial or biaxial stretching. Stretching in more than one direction, such as biaxial stretching, may be accomplished simultaneously or sequentially. For example, when sequential biaxial stretching a film of shape deformation material, the first or initial stretching can be conducted in either the machine direction (MD) or the transverse direction (TD) of the film material.

In one embodiment of the present invention, the treated material desirably possesses a draw or stretch ratio of at least 1.5 in one or more directions. More desirably, the treated material possesses a draw or stretch ratio in one or more directions of from about 2 to about 10. Even more desirably, the treated material possesses a draw or stretch ratio in one or more directions of from about 3 to about 7. Lower draw ratios may result in low shape deformation and low recoverable deformation. However, low draw ratios may be applicable to some embodiments of the present invention, depending on specific applications and the desired amount of shape deformation. Very high draw ratios during the process of imparting shape-deformation memory may result in a partial loss of shape memory as a result of unrecoverable plastic deformations in the material.

Stretching Temperature

During stretching, the material sample may be optionally heated. Desirably, stretching is conducted at temperatures below the melting temperature of the material. In one embodiment of the present invention wherein the material is a polymeric material, the drawing temperature is not more than about 120° C. and, desirably, not more than about 90° C. When the drawing temperature is too high, the material can melt, become excessively tacky, and/or become difficult to handle. In addition, excessively high stretching temperatures can cause irreversible deformations in which the shape deformation of the material is lost and the original shape is not recoverable.

Stretching a given material at low temperatures may result in a lower amount of locked-in shape deformation and low percent recovery during activation. Generally, when the shape deformation material comprises segmented block thermoplastic elastomers, it is desired to stretch the material near the softening or glass transition temperature of the hard segments. In some cases, when the soft segments experience strain induced crystallization during stretching, drawing the material near the crystalline transition temperature of the soft segments is desired. This is the case, for example, when the shape deformation material is a PEBAX® elastomer.

Stretch Rate

The rate at which stretching is performed may also affect the amount of locked-in shape deformation imparted to a given shape deformation material. Suitable stretching rates will vary depending upon the material to be stretched. As a general rule, stretching may be accomplished at rates of at least about 50%/min. and as much as about 5000%/min. Desirably, the stretching rate is from about 100%/min. to about 2500%/min. Higher stretching rates may be more beneficial for process efficiency; however, very high stretching rates may result in a material failure at reduced draw ratios. The effect of stretching rate on locked-in shape deformation is dependent upon the structure and composition of the material. For some embodiments of the present invention, such as when the shape deformation material comprises a thermoplastic polyurethane, the stretching rate does not have a significant impact on the resulting amount of locked-in shape deformation.

Post-Stretching Operations

The locked-in shape deformation properties of a shape deformation material of the present invention may be affected by post-stretching operations. A number of factors should be considered during post-stretching operations including, but not limited to, the material composition, the relaxation tendency of the material, and the desired amount of percent recovery for a particular application.

Relaxation Tendency

In most cases, the shape deformation material will possess a tendency to return to its original, pre-stretched configuration. This property may be described as a relaxation tendency. Although the relaxation tendency may vary from material to material, generally, the amount of relaxation tendency increases as the elasticity of the material increases. Further, the amount of relaxation tendency increases for a given material as the temperature of the material increases.

Tension

During post-stretching operations, the stretched material may be held under tension in a stretched state, gradually released from a stretched state over time, or treated in some manner while in a tensionless state. Typically, recoverable shape deformation or percent recovery is larger when the shape deformation material is held in a stretched state for a longer period of time. When the shape deformation material is a polymeric fiber or film, the shape deformation material is desirably held in a stretched state for at least about 30 seconds. More desirably, the shape deformation material is held in a stretched state for at least about ten minutes. Even more desirably, the shape deformation material is held in a stretched state for at least about one hour, and most desirably, about 24 hours. The time under tension depends on a molecular structure of the shape deformation polymer. For poly(ether amide) shape deformation elastomer, e.g. PEBAX® elastomer, the material can be held under tension for a very short period of time. For polyester aromatic and aliphatic polyurethanes with shape deformation, e.g. MORTHANE® polyurethanes, a longer time under tension is preferred. The use of tension, especially in combination with temperature, may be useful to preserve orientation in the shape deformation material and protect the resulting structure against undesirable shrinkage after stretching.

Temperature

The stretched shape deformation material may be subjected to post-stretching operations at room temperature or at elevated temperatures. The "setting" process (i.e., the process of locking-in a desired amount of stretch) may be conducted in accordance with a selected, predetermined temperature-time profile, which is dependent on the structure of the shape deformation material and the relaxation tendency of the shape deformation material. In general, the setting process is conducted at temperatures below the melting temperature of the shape deformation material. Desirably, the setting process is conducted at temperatures above the temperature of secondary relaxation processes and temperatures above the glass transition temperature of the soft segments in segmented block elastomers. This allows the sturcture to relax during the setting process and reduce relaxation tendency, which can result in increased shape deformation It is important to note that initial material temperature may be important to provide the most efficient coupling of EMR energy with the molecular structure of the material. Cooling down the shape deformation material or preheating it before EMR treatment, which depends on the specific molecular arrangement and composition of a material, can shift the molecular-dipole relaxation times in the frequency range of the EMR application system, which typically operates in a frequency range of about $10^9$ Hz. This cooling or preheating can significantly enhance a coupling of the EMR energy with the molecular structure of the shape deformation material and can increase the activation efficiency of the EMR energy. In addition to dipole relaxation, or in place of dipole relaxation, ionic conductivity or ionic mobility can be utilized for activation by EMR energy.

Other Post-Stretching Operations

Other additional post-stretching processes or operations, such as UV treatment, ultrasonic treatment, high energy treatment, or combinations of these treatments, may be incorporated into the post-stretching process to modify the morphological state of the stretched material and to maximize the percent recovery of the shape deformation material upon activation.

The Activation Process

The present invention is further directed to a method of causing the efficient recovery of at least a portion of the latent, locked-in shape deformation of the above-described shape deformation materials. The method comprises subjecting the shape deformation material to an amount of activation energy in order to effect a substantial change (i.e., recovery) in at least one spatial dimension of the material. The method may be used to cause the shape deformation of the above-described shape deformation material itself or a product containing as one or more components the above-described shape deformation material.

Recovery of latent, locked-in shape deformation of the shape deformation material of the present invention is accomplished by exposing the shape deformation material to an amount of activation energy having a desired frequency and power level. Desirably, the activation energy comprises electromagnetic radiation (EMR) having a frequency range of from about 10 MHz to about 30 GHz. More desirably, the activation energy comprises electromagnetic radiation (EMR) having a frequency range of from about 20 MHz to about 2500 MHz.

The shape deformation material of the present invention may be exposed to a sufficient amount of activation energy to effect a change in at least one spatial dimension of the material. Desirably, the shape deformation material exhibits a desired amount of percent recovery upon exposure to electromagnetic radiation (EMR) for less than about three seconds. More desirably, the shape deformation material exhibits a desired amount of percent recovery upon exposure to electromagnetic radiation (EMR) for less than about one second. Even more desirably, the shape deformation material exhibits a desired amount of percent recovery upon exposure to electromagnetic radiation (EMR) for less than about 0.5 seconds. Even more desirably, the shape deformation material exhibits a desired amount of percent recovery upon exposure to electromagnetic radiation (EMR) for less than about 0.05 seconds.

As shown by example in FIG. 4, an optimum percent recovery range may be determined for a given shape deformation material and a given activation energy unit. The combined effects of a power level of a given activation energy unit and the speed of the shape deformation material through the activation energy unit lead to a variety of results including inefficient recovery of a sample, melting of the sample, and desired recovery of the sample. As shown in FIG. 4, when the speed is low (i.e., the residence time is long), the sample absorbs too much energy and melts as it passes through the unit. If the speed is too high and the power too low, the residence time is too short and the sample cannot absorb enough energy to be activated. Optimization occurs within the diagonal region on FIG. 4 from about medium speed/medium power to high speed/high power. Because this diagonal region appears to be linear, it is believed that for at least some shape deformable materials high recoveries at high web speeds is only limited by the microwave power available and the ability of the shape deformable material to absorb microwave energy at a high rate. The shape deformable material can be designed to allow a high rate of EMR absorption.

Percent recovery may vary depending on a number of factors including, but not limited to, the shape deformation material; the amount of latent, locked-in shape deformation; the pre-activation treatments used to prepare the shape deformation material; and the desired amount of percent recovery for a particular application. For most applications, the percent recovery (%R) is desirably greater than about 30% upon exposure to EMR energy for less than about one second. For most applications, the percent recovery (%R) is more desirably greater than about 60% upon exposure to EMR energy for less than about one second. A preferred range of the percent recovery is from about 15% to about 75% upon exposure to EMR energy for less than about one second.

As discussed above, the use of EMR energy in the present invention to activate shape deformation materials is advantageous over conventional methods, which use thermal energy, for a number of reasons. The use of EMR energy enables rapid molecular reorientation (i.e., recovery) of a shape deformable material having a latent, locked-in amount of shape deformation without a substantial increase in the temperature of the shape deformable material. As used herein, "a substantial increase in the temperature of the shape deformable material" refers to an increase in temperature of greater than about 15° C. Desirably, the shape deformable material exhibits a desired percent recovery while experiencing a temperature change of less than about 12° C. More desirably, the shape deformable material exhibits a desired percent recovery while experiencing a temperature change of less than about 10° C. Even more desirably, the shape deformable material exhibits a desired percent recovery while experiencing a temperature change of less than about 8° C. Even more desirably, the shape deformable material exhibits a desired percent recovery while experiencing a temperature change of less than about 5° C.

As opposed to conventional recovery methods, which desire thermal heating of a shape deformable material, the activation process of the present invention desirably minimizes the degree of heating of the shape deformable material. Further, the activation process of the present invention results in no surface overheating of the shape deformation material, controlled energy delivery, short exposure times, increased throughput, reduced material degradation, and energy savings. Additionally, activation with EMR energy advantageously occurs in a fraction of the time required for hot air or convection oven activation using heat. Such conventional processes require from as few as about 10 seconds to as great as about 15 to 20 minutes for activation depending upon the particular article or configuration. These processes require such relatively long activation times because of the need to transfer heat from the surface of the article to the interior of the article and because the heat conductivity of the article, and dry air surrounding the article, is poor. In contrast to the activation times of conventional processes, the activation period in the present invention may be lower than 0.01 seconds.

In some conventional processes, the recovery of shape deformation is achieved by heating a shape deformable material to temperatures below the melting temperature of the stretched polymer material and above the stretching temperature. Low recovery temperatures may result in low recoverable deformation, while excessively high temperatures may result in melting of the shape-deformed material. However, in the present invention using EMR radiation, the temperature of the environment is not critical. The temperature of the environment surrounding the shape deformable material of the present invention may vary depending on the desired conditions in a given room. For example, the activation process of the present invention may be performed at room temperature or in a cooled or heated zone.

The EMR treatment used in the present invention may be provided, for example, by multi-mode, traveling wave, or single mode resonating cavity applicators. A suitable microwave generator and cavity is described in U.S. Pat. No. 5,536,921 to Hedrick et al. and U.S. Pat. No. 5,916,203 to Brandon et al., which are hereby incorporated by reference. Such a generator typically provides a plurality of microwave standing waves within an enclosure or cavity. The web of material can then be passed through the standing waves where the incident microwave energy can be utilized within the web. Microwave energy may then be supplied, continuously or intermittently, to the continuously moving web of microwave sensitive material at a rate, which activates the selected regions on the web. The rate at which the energy is supplied is dependent upon the type of material and the speed at which the composite material is moving. A generator may also be configured to provide a variable amount of microwave energy relative to the speed of the web such that the energy provided increases as the web speed increases. To provide such high levels of energy in such a short time period, it may be desirable to have more than one microwave cavity through which the web passes. For example, in one embodiment, the system used in the present invention may include from two to twenty cavities through which the web passes to provide the necessary energy to activate the selected regions on the web of material.

Alternatively, the EMR may be applied using a radio frequency (RF) generator which would provide a uniform distribution of activation energy through the shape deformation material. A suitable RF system is described in U.S. Pat. No. 4,675,139 to Kehe et al., which is incorporated herein by reference. Another suitable RF system is described in U.S. Pat. No. 5,950,325, which is also incorporated herein by reference. In this type of system, the material is passed between two metal plates or electrodes. A generator applies to the plates a high-frequency current of 1 to 200 megahertz that sets up an electric field in and around the material. The web of material can then be passed through this field where the incident RF energy can be utilized by the web.

The energy input in a RF activation system may be precisely controlled since the voltage across the capacitor plates and the gap between the plates are adjustable for optimum energy input. Further, the process can be arranged in such a way that the capacitor plates and/or plate electrodes provide energy into the system, as well as, provide compaction or molding pressure on the shape deformation material. In other words, the capacitor plates and/or plate electrodes may be used to press the shape deformation material to a desired thickness or shape while supplying activation energy to the shape deformation material. In a further embodiment, the capacitor plates and/or plate electrodes may be in the form of pressure rolls, which can provide activation energy, compaction, and transport of the activated product resulting in enhanced processing speeds and a reduction in processing costs.

In one embodiment of the present invention, the desired EMR application system is a National GEN6KWCONTROLA remote control unit coupled to a Spellman MG1 0 series switch-mode power supply. These units power a 2450 MHz microwave generator from Richardson Electronics. The microwaves can be passed through a directional coupler, waveguide, and stub tuner to a single mode resonating cavity. Forward and reflected power in the system may be adjusted and optimized for various materials through adjustments to the generator control and stub tuner.

The activation process of the present invention may be performed in a batch or continuous operation. Desirably, the activation process is a continuous process, such as the process shown in FIG. 1, wherein a composite material 10 is subjected to EMR. The composite material 10 comprises a web of material 12 having numerous shape deformation materials 14 thereon. The composite material 10 passes through EMR wave cavity 18 to activate shape deformation material 14 and covert shape deformation material 14 into recovered material 16. Generator 60 supplies EMR energy having a desired frequency range and power level. The speed of composite 10 determines the exposure time of shape deformation material 14.

The activation process of the present invention may be performed using one or more of the above-mentioned EMR-generating apparatus in a continuous operation. For example, one or more microwave generators may be used in combination with one or more radio wave generators. Further, one or more microwave generators and/or one or more radio wave generators may be used in combination with one or more conventional apparatus such as infrared, ultraviolet, electron beam, or heated air activation systems.

Compared to conventional systems, which have used heated air or heated rolls to activate webs or individual pieces of latent elastic material, the use of EMR energy is less expensive, easier to control, and faster to provide improved manufacturing efficiency and quality. For example, in a manufacturing process for absorbent articles such as diapers, the entire diaper article may be manufactured and packaged while the shape deformation material of the absorbent article is in a latent state. Prior to shipping the articles, the shape deformation material within the absorbent article may be activated by EMR energy as shown in FIG. 1.

Articles of Manufacture

The present invention is further directed to articles of manufacture, which contain the above-described shape deformable materials. The shape deformable material may represent a substantial part of the article of manufacture or may represent one of many components of the article. Further, the shape deformable material may be used as a single layer component or may be present as one layer of a multi-layer laminate within the article of manufacture. Suitable articles of manufacture include, but are not limited to, products containing an elastic portion, such as diapers, as well as, products having a shrinkable, gatherable or expandable component.

In one embodiment of the present invention, the shape deformable material is in the form of a film, which is laminated to one or more additional layers to form a composite article. The additional layers may comprise additional films, nonwoven webs, woven fabrics, foams, or a combination thereof. The resulting laminated article is suitable for use in a number of applications, such as disposable absorbent products. Such products include, but are not limited to, absorbent personal care items such as diapers, training pants, adult incontinence products, feminine care products such as sanitary napkins and tampons, and health care products such as wound dressings. Other products include surgical drapes, surgical gowns, and other disposable garments.

The composite material of this embodiment is representatively illustrated in FIG. 2. As can be seen in FIG. 2, the composite material 20 comprises a nonwoven web layer 22; and strips of shape deformable material 24 and 26, which are attached to layer 22. The strips of shape deformable material 24 and 26 may be attached to nonwoven web layer 22 by any means known to those of ordinary skill in the art. Depending on the amount and degree of latent, locked-in shape deformation within the strips of shape deformable material 24 and 26, activation of the composite material results in a desired gathered composite material.

One article of manufacture of particular interest is an absorbent garment article representatively illustrated in FIG. 3. As can be seen in FIG. 3, the absorbent garment may comprise a disposable diaper 30, which includes the following components: a front waist section 31; a rear waist section 32; an intermediate section 33, which interconnects the front and rear waist sections; a pair of laterally opposed side edges 34; and a pair of longitudinally opposed end edges 35. The front and rear waist sections include the general portions of the article, which are constructed to extend substantially over the wearers front and rear abdominal regions, respectively, during use. The intermediate section 33 of the article includes the general portion of the article, which is constructed to extend through the wearer's crotch region between the legs. The opposed side edges 34 define leg openings for the diaper and generally are curvilinear or contoured to more closely fit the legs of the wearer. The opposed end edges 35 define a waist opening for the diaper 30 and typically are straight but may also be curvilinear.

FIG. 3 is a representative plan view of a diaper 30 of the present invention in a flat, uncontracted state. Portions of the structure are partially cut away to more clearly show the interior construction of the diaper 30, and the surface of the diaper which contacts the wearer is facing the viewer. The diaper 30 further includes a substantially liquid impermeable outer cover 36; a porous, liquid permeable bodyside liner 37 positioned in facing relation with the outer cover 36; an absorbent body 38, such as an absorbent pad, which is located between the outer cover and the bodyside liner; and fasteners 42. Marginal portions of the diaper 30, such as marginal sections of the outer cover 36, may extend past the terminal edges of the absorbent body 38. In the illustrated embodiment, for example, the outer cover 36 extends outwardly beyond the terminal marginal edges of the absorbent body 38 to form side margins 40 and end margins 41 of the diaper 30. The bodyside liner 37 is generally coextensive with the outer cover 36, but may optionally cover an area, which is larger or smaller than the area of the outer cover 36, as desired.

Shape deformable material as described above may be incorporated into various parts of the diaper 30 illustrated in FIG. 3. Desirably, a pair of laterally opposed side strips 44 and/or a pair of longitudinally opposed end strips 46 comprise the shape deformable material of the present invention. Upon activation, strips 44 and 46 form gathered portions, which provide a snug fit around the waist and leg openings of the diaper 30.

Optimizing Interaction of Polymer With EMR Energy

The present invention is also directed to a method of making shape deformable polymers in an effort to optimize the interaction of the shape deformable polymer with a selected activation energy. By incorporating one or more selected moieties into the polymer backbone and/or positioning one or more selected moieties at strategic sites along the polymer backbone of the shape deformable polymer, one can tailor a specific shape deformable polymer, which will optimally respond to a selected activation energy, such as electromagnetic energy (EMR) having a specific wavelength.

For shape deformable polymers, the efficiency of EMR absorption is related to the dielectric properties of the polymer. Typically, a shape deformable polymer suitable for use in the present invention demonstrates a high dielectric loss factor in a frequency range corresponding to the EMR energy. Desirably, the shape deformable polymer has a dielectric loss factor at a given frequency within the EMR frequency range of from about 10 MHz to about 30 GHz of greater than about 0.05. More desirably, the shape deformable polymer has a dielectric loss factor at a given frequency within the EMR frequency range of from about 10 MHz to about 30 GHz of greater than about 0.1. Even more desirably, the shape deformable polymer has a dielectric loss factor at a given frequency within the EMR frequency range of from about 10 MHz to about 30 GHz of greater than about 0.20. Even more desirably the shape deformable polymer has a dielectric loss factor at a given frequency within EMR frequency range of from about 10 MHz to about 30 GHz of greater than about 0.25.

By increasing the dielectric loss factor of a synthesized shape deformable polymer, one can increase the responsiveness of the polymer to electromagnetic energy having a specific wavelength. As discussed above with regard to functional groups within a shape deformable polymer, specifically selected moieties along the polymer chain and the positioning of moieties along the polymer chain can effect the dielectric loss factor of the shape deformable polymer, and enhance the responsiveness of the polymer to electromagnetic energy. Desirably, the presence of one or more moieties along the polymer chain causes one or more of the following: (1) an increase in the dipole moments of the polymer; and (2) an increase in the unbalanced charges of the polymer molecular structure. Suitable moieties include, but not limited to, aldehyde, ester, carboxylic acid, sulfonamide and thiocyanate groups.

The selected moieties may be covalently bonded or ionically attached to the polymer chain. As discussed above, moieties containing functional groups having high dipole moments are desired along the polymer chain. Suitable moieties include, but are not limited to, urea, sulfone, amide, nitro, nitrile, isocyanate, and ketone groups. Other suitable moieties include moieties containing ionic groups including, but are not limited to, sodium, zinc, and potassium ions.

One example of modifying a polymer chain to enhance the responsiveness of the polymer chain is shown below:

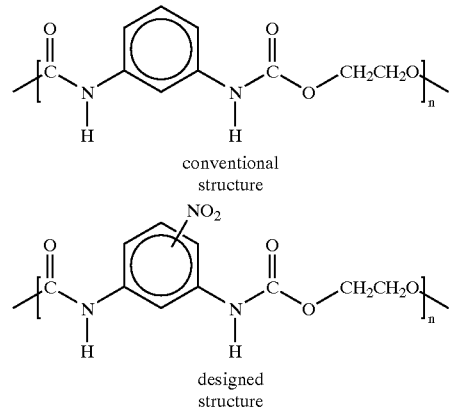

conventional structure designed structure

In the above example, a nitro group is attached to the aryl group within the polymer chain. It should be noted that the nitro group may be attached at the meta or para position of the aryl group. Further, it should be noted that other groups may be attached at the meta or para position of the aryl group, as shown above, in place of the nitro group. Suitable groups include, but are not limited to, nitrile groups. In addition to the modification shown above, one could incorporate other monomer units into the polymer above to further enhance the responsiveness of the resulting polymer. For example, monomer units containing urea and/or amide groups may be incorporated into the above polymer.

A further example of designing a shape deformable polymer is given below, wherein one or more moieties, X and Y, are bonded to specific sites along a block copolymer chain:

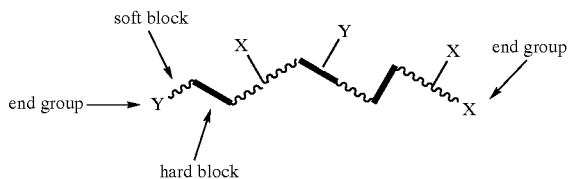

X and Y may be bonded on soft blocks, hard blocks, or both soft and hard blocks, as well as, on the ends of the polymer chain. X and Y may be randomly bonded or uniformly bonded along the polymer chain. Suitable moieties include aldehyde, ester, carboxylic acid, sulfonamide and thiocyanate groups. However, other groups having or enhancing unbalanced charges in a molecular structure can also be useful; or a moiety having an ionic or conductive group such as, e.g., sodium, zinc, and potassium ions. However, other ionic or conductive groups can also be used.

It should be noted that moieties X and Y may also be bonded to the same soft or hard block within a given polymer chain. In one embodiment shown below, X and Y are bonded to the same soft or hard block within a given polymer, wherein X is a moiety having a positive charge and Y is a moiety having a negative charge:

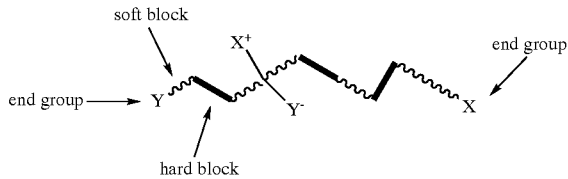

In such a configuration, the unbalanced charge within one polymer segment results in enhanced interaction between the polymer and electromagnetic radiation.

A further method of optimizing the interaction of a given polymer and an electromagnetic field is to identify a maximum dielectric loss factor of the polymer along the frequency range of the electromagnetic field. By identifying a maximum dielectric loss factor value of a shape deformable polymer at a specific frequency within the EMR frequency range of from about 10 MHz to about 30 GHz, one can subject the shape deformable polymer to an activation energy at the specific frequency corresponding to the maximum dielectric loss factor of the polymer.

Figure 6:
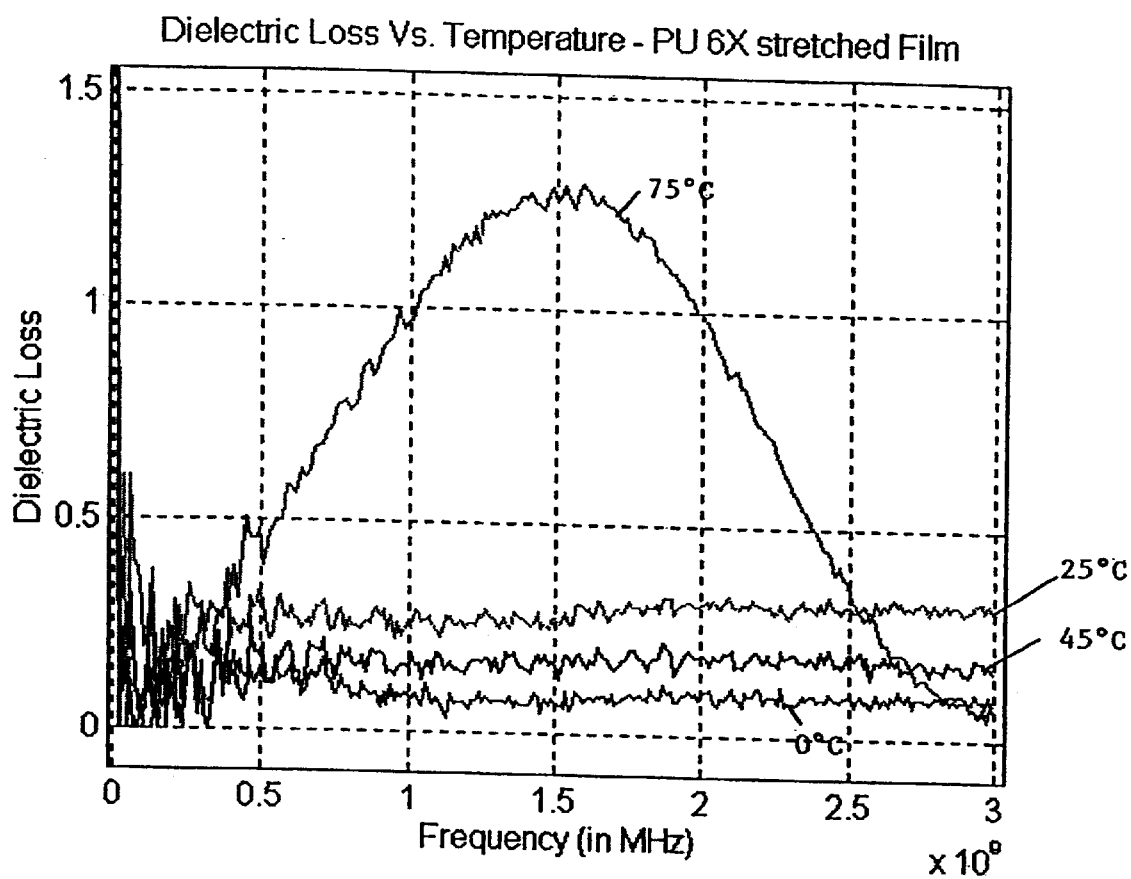
FIG. 6 graphically displays the change in value of the dielectric loss factor of polyurethane versus frequency at selected temperatures.

Other factors may be considered when optimizing process conditions during a recovery process. For example, the dielectric loss factor of a shape deformable polymer may be significantly influenced by the temperature of the polymer. For illustrative purposes only, FIGS. 5 and 6 graphically display the change in value of the dielectric loss factor of two polymers versus frequency at selected temperatures. FIG. 5 graphically displays the change in value of the dielectric loss factor of polyether amide copolymer, PEBAX® 2533 film, stretched 6×, versus frequency at temperatures of 0° C., 25° C., 45° C., and 75° C. FIG. 6 graphically displays the change in value of the dielectric loss factor of polyurethane, MORTHANE® PS370-200 film, stretched 6×, versus frequency at temperatures of 0° C., 25° C., 45° C., and 75° C. The stretched PEBAX® 2533 film demonstrated a dramatic increase in dielectric loss factor at a temperature of 75° C. in a frequency range from about 0.25 GHz to about 2.5 GHz with a maximum loss factor of about 5 at about 1 GHz as illustrated in FIG. 5. The stretched MORTHANE® PS370-200 film demonstrated a dramatic increase in a dielectric loss factor at a temperature of 75° C. in a frequency range from about 0.5 GHz to about 2.4 GHz with a maximum loss factor of about 1.25 at about 1 GHz as illustrated in FIG. 6. These data show that shape deformation materials can exhibit a significant dependence of a dielectric loss factor upon frequency of EMR and a preheating of the material. This finding can provide an insight into a better design of a microwave application system in terms of preferred frequency range and preconditioning of the shape deformation materials.

As discussed above, EMR absorbers may be combined with a specifically designed shape deformable polymer to further enhance the interaction of the polymer with electromagnetic radiation.

The present invention is further described by the examples which follow. Such examples, however, are not to be construed as limiting in any way either the spirit or scope of the present invention. In the examples, all parts are parts by weight unless stated otherwise.

EXAMPLES

The following examples were conducted to produce shape deformation materials having an amount of locked-in shape deformation, and to activate the materials. Degree of stretch/stretch ratio, stretch rate, and stretch hold/cooling rate were some of the factors considered in order to introduce the most latent, lock-in shape deformation.

Materials

Two types of polyester-based aromatic thermoplastic polyurethanes and one type of polyester aliphatic polyurethane were tested, all supplied by Morton International (Chicago, Ill.). The first polyurethane, MORTHANE® PS370-200 (melt index MI=5, shore hardness 78, 100% tensile modulus 3.4 MPa (500 psi)) was chosen for its good elastic properties, its low modulus, high strength and its soft feel. The second polyurethane, MORTHANE® PS79-200 (melt index MI=20, shore hardness 85, 100% tensile modulus 5.9 MPa (850psi)) was chosen for its good processability and reduced tackiness. The third polyurethane, which was the polyester aliphatic polyurethane, was MORTHANE® PN3429-219 (melt index MI=50) and was selected for its good processability. Each polyurethane was obtained in pellet form and extruded into films using a Haake twin-screw extruder. Before extruding into a film, the resin was dried at 80° C. for MORTHANE® PS370-200, at 60° C. for MORTHANE® PS79-200 and 50° C. for MORTHANE® PN3429-219. The extruded films had a thickness of approximately 2 mil.

Test Procedures

The following test procedures were used to determine properties of the films.

Dielectric Properties

Dielectric measurements were made using a Network Analyzer capable of generating a low power (0 to +5 dBm) swept Radio Frequency (RF) signal over a frequency range of 300 kHz to 3 GHz. Samples of single fold (i.e. two layer) thickness are placed in contact with a coaxial probe yielding low-loss resolution measurements for solid films. Specifically, an HP 8752C (300 kHz to 3 GHz) RF Network Analyzer, and an HP 85070B Reflectance Dielectric Probe are used for the dielectric determinations. Once calibrated, the instrument is used to directly measure dielectric constant (e'), and dielectric loss factor (e"). From this information, calculations can be made for power dissipation factor (loss tangent, e"/e'). All calculations and graphical presentations were performed using MatLab (Matrix Laboratory) software from The Mathworks, Natick, Mass. The various temperature measurements were made by placing the film on a ceramic block maintained at the appropriate temperature during measurement.

The dielectric data (e', e" and e"/e') for four different samples are provided below. Sample 1 is polyester aliphatic polyurethane, PN3429-219. Sample 2 is polyester aromatic polyurethane, PS370-200. Sample 3 is PEBAX® polyether amide copolymer 2533—film stretched 6× at room temperature. Sample 4 is polyurethane, PS370-200 film stretched 6× at 80° C.

|  | MHz | e' | e" | e"/e' |
|---|---|---|---|---|
| Sample 1 |  |  |  |  |
| 0° C. | 27.1 | 1.21 | 0.12 | 0.099174 |
|  | 915 | 1.799457 | 0.08806 | 0.048937 |
|  | 2450 | 1.761119 | 0.087892 | 0.049907 |
| 25° C. | 27.1 | 2.76 | 0.604 | 0.218841 |
|  | 915 | 2.346763 | 0.147718 | 0.062945 |
|  | 2450 | 2.233475 | 0.137417 | 0.061526 |
| 45° C. | 27.1 | 2.14 | 0.15 | 0.070093 |
|  | 915 | 2.00048 | 0.10122 | 0.050598 |
|  | 2450 | 1.905912 | 0.115385 | 0.060541 |
| 75° C. | 27.1 | 3.72 | 0.241 | 0.064785 |
|  | 915 | 2.952051 | 0.260132 | 0.088119 |
|  | 2450 | 2.714274 | 0.266041 | 0.098016 |
| Sample 2 |  |  |  |  |
| 0° C. | 27.1 | 1.14 | 0.441 | 0.386842 |
|  | 915 | 1.723 | 0.077036 | 0.04471 |
|  | 2450 | 1.674601 | 0.096932 | 0.057884 |
| 25° C. | 27.1 | 3.39 | 0.277 | 0.081711 |
|  | 915 | 2.963203 | 0.219667 | 0.074132 |
|  | 2450 | 2.794656 | 0.252468 | 0.09034 |
| 45° C. | 27.1 | 2.56 | 0.11 | 0.042969 |
|  | 915 | 2.137411 | 0.123166 | 0.057624 |
|  | 2450 | 2.020432 | 0.131741 | 0.065204 |
| 75° C. | 27.1 | 2.51 | 0.13 | 0.051793 |
|  | 915 | 1.884419 | 0.131057 | 0.069548 |
|  | 2450 | 1.79201 | 0.113719 | 0.063459 |
| Sample 3 |  |  |  |  |
| 0° C. | 27.1 | 2.32 | 0.31 | 0.133621 |
|  | 915 | 2.181792 | 0.13449 | 0.061642 |
|  | 2450 | 2.101588 | 0.137296 | 0.06533 |
| 25° C. | 27.1 | 3.48 | 0.14 | 0.04023 |
|  | 915 | 2.86928 | 0.153418 | 0.053469 |
|  | 2450 | 2.749838 | 0.20396 | 0.074172 |
| 45° C. | 27.1 | 2.28 | 0.19 | 0.083333 |
|  | 915 | 2.218893 | 0.190131 | 0.085687 |
|  | 2450 | 2.094158 | 0.173597 | 0.082896 |
| 75° C. | 27.1 | 2.9 | 1.1 | 0.37931 |
|  | 915 | 2.279023 | 5.011064 | 2.198777 |
|  | 2450 | 2.063194 | 0.800902 | 0.388186 |
| Sample 4 |  |  |  |  |
| 0° C. | 27.1 | 1.4 | 0.385 | 0.275 |
|  | 915 | 1.779433 | 0.09235 | 0.051899 |
|  | 2450 | 1.710493 | 0.095685 | 0.05594 |
| 25° C. | 27.1 | 4.27 | 0.56 | 0.131148 |
|  | 915 | 3.544206 | 0.293757 | 0.082884 |
|  | 2450 | 3.351744 | 0.310472 | 0.09263 |
| 45° C. | 27.1 | 3.34 | 0.19 | 0.056886 |
|  | 915 | 2.435807 | 0.182267 | 0.074828 |
|  | 2450 | 2.295267 | 0.176522 | 0.076907 |
| 75° C. | 27.1 | 2.79 | 0.48 | 0.172043 |
|  | 915 | 3.440623 | 0.914258 | 0.265725 |
|  | 2450 | 2.410955 | 0.394036 | 0.163436 |

As can be seen from the data, the high dielectric losses of the materials over the broad range of frequencies shows that the materials may be activated by EMR in the RF and/or microwave frequency ranges. For example, each of the samples had a higher dielectric loss as measured at 25° C. and 27.1 MHz than as measured 25° C. and 2450 MHz. Additionally, the higher dielectric loss factor at 27.1 MHz suggests that these materials will EMR in the RF range than in the microwave Streching Procedures to Impart Latent Deformation An MTS Sintech 1/D instrument equipped with a 50-pound load cell and an environmental chamber was used to stretch the sample to impart a desired amount of shape deformation. Samples of each film were cut 1" wide by 3" to 4" long and were labeled and marked in black ink with lines 20 mm apart. Samples were then placed in the grips of the MTS Sintech 1/D instrument spaced 2" apart and stretched a desired amount. Samples were stretched from 3× (i.e., three times the original length) to more than 6×, at a desired stretch rate. Stretch rates were either 100 mm/min (i.e., the "slow" rate) or 500 mm/min (i.e., the "fast" rate). When necessary, the grips and sample were placed in the environmental chamber and heated to a desired temperature, which varied from about 37° C. to about 100° C., allowed to equilibrate, and then stretched the desired amount at the desired rate.

Unless otherwise noted, after stretching, the sample was held stretched at the stretching temperature for 1 minute. Then, the sample was cooled by one of two methods. "Slow cooling" was one method wherein the environmental chamber door was opened and the stretched sample exposed to a fan until the sample had reached room temperature at which point the sample was released from the stretched position and removed. The other method was "quenching," wherein the environmental chamber door was opened and the sample was sprayed with a cooling agent (i.e., Blow-Off freeze spray comprising 1,1,1,2-tetrafluoroethane) for a number of passes while the sample was released from the stretched position and removed from the chamber.

The distance between the lines was measured and recorded and new lines were marked in red 20 mm or 40 mm apart depending upon the sample length. Latent, locked-in shape deformation, or percent latency, was defined as the change in length from the stretched sample to the initial sample, divided by the initial sample length, and multiplied by 100.

Procedure For Measuring Temperature During Activation

The temperature of sample films exposed to microwave radiation was determined as follows. An infrared imaging camera having the following specifications was used to detect the surface temperature of the sample films:

| Camera: | Agema ThermaCam PM595 |
|---|---|
| Detector: | microbolometer, 7.5–13 $\mu$m response |
| Accuracy: | +/− 2° C., +/− 2% |
| Range: | −40° C. to 1500° C. |
| Field of View (FOV): | 24° × 18° |
| Minimum Focus Distance ($FD_{min}$): | 0.5 m |
| Array Size: | 320 × 240 pixels |

The camera was set up on the microwave unit at a location about 7 inches from the exit of the microwave application cavity and about 18 inches above the film sample.

Rectangular strips of film were placed on a polypropylene web having a very low absorption of microwaves. The used polypropylene web was PP nonwoven with dielectric properties measured at room temperature of 25° C. and frequency of 2450 MHz being: e"=1.37 and e"=0.0166. The dielectric loss factor, e", was about one order of magnitude (10 times) lower compared to activatable, microwave responsive shape deformation materials. Low loss factor for PP nonwoven web suggests a very low absorption of microwaves. To ensure that the temperatures measured by the camera were accurate, film samples were run through the microwave cavity without exposure to microwave radiation. The film samples were found to have an average temperature of 25.5° C., within 2° C. of room temperature.

Film samples were then run through the microwave cavity at a variety of speeds and power levels. Images of the film samples were taken and stored on flash memory cards as the film samples exited the microwave cavity. Using the camera's temperature analysis software, temperature information was collected for each sample.

Example 1

Effect of Stretch Rate on the Amount of Locked-in Shape Deformation

Rectangular strips of MORTHANE® PS 370-200 were stretched using a slow stretch rate and a fast stretch rate. The strips were stretched up to 6 times their initial length at three separate temperatures, 25° C., 50° C., and 70° C. using a Sintech tensile tester (SINTECH 1/D) and an environmental chamber.

The results of the tests are given below in Table 1.

TABLE 1

Stretch Rate Results

| Temperature | 25° C. | | 50° C. | | 70° C. | |
|---|---|---|---|---|---|---|
| Stretch Rate | Slow | Fast | Slow | Fast | Slow | Fast |
| % Latency | 15 | 20 | 75 | 75 | 145 | 150 |

As can be seen in Table 1, the stretch rate did not significantly effect the percent latency of MORTHANE® PS 370-200. However, the temperature had a significantly effect on the percent latency of MORTHANE® PS 370-200.

Example 2

Effect of Draw Ratio on the Amount of Locked-in Shape Deformation

Rectangular strips of MORTHANE® PS 370-200 were stretched using three different draw ratios: 4x, 5x, and 6x. The strips were stretched at three separate temperatures, 25° C., 50° C., and 70° C. using a Sintech tensile tester (SINTECH 1/D) and an environmental chamber.

The results of the tests are given below in Table 2.

TABLE 2

Draw Ratio Results

| Temperature | 25° C. | | | 50° C. | | | 70° C. | | |
|---|---|---|---|---|---|---|---|---|---|
| Draw Ratio | 4x | 5x | 6x | 4x | 5x | 6x | 4x | 5x | 6x |
| % Latency | 15 | 15 | 25 | 80 | 120 | 75 | 125 | — | 150 |

As can be seen in Table 2, the draw ratio did not significantly effect the percent latency of MORTHANE® PS 370-200.

Example 3

Effect of Stretch Temperature on the Amount of Locked-in Shape Deformation

Rectangular strips of MORTHANE® PS 370-200 were stretched using three different temperatures: 25° C., 50° C., and 70° C. The strips were stretched at two different draw ratios, 4x and 6x, using a Sintech tensile tester (SINTECH 1/D) and an environmental chamber.

The results of the tests are given below in Table 3.

TABLE 3

Temperature Results

| Temperature | 25° C. | | 50° C. | | 70° C. | |
|---|---|---|---|---|---|---|
| Draw Ratio | 4x | 6x | 4x | 6x | 4x | 6x |
| % Latency | 15 | 25 | 80 | — | 125 | 150 |

As can be seen in Table 3, the stretch temperature had a significantly effect on the percent latency of MORTHANE® PS 370-200.

Example 4

Effect of Stretch Hold and Cooling Rate on the Amount of Locked-in Shape Deformation Rectangular strips of MORTHANE® PS 370-200 were stretched at different temperatures: 70° C. and 90° C. The strips were stretched at a draw ratio of 6x, using a Sintech tensile tester (SINTECH 1/D) and an environmental chamber. The samples were either slowly cooled or quenched as described above. The samples were allowed to cool or quenched after being held in a stretched position for one minute, and also without being held.

The results of the tests are given below in Table 4.

TABLE 4

Stretch Hold/Cooling Rate Results

| Temperature | 70° C. | | | | 90° C. | | | |
|---|---|---|---|---|---|---|---|---|
| Stretch Hold | Load | | No Load | | Load | | No Load | |
| Cooling Method | SC | Q | SC | Q | SC | Q | SC | Q |
| % Latency | 145 | 145 | 140 | 150 | 235 | 180 | 210 | 190 |

As can be seen in Table 4, the MORTHANE® PS 370-200 samples had a larger amount of percent latency when slowly cooled after being held for one minute at a given stretch temperature and then allowed to cool as opposed to the samples allowed to cool without being held. Quenching reduced the amount of time the samples were held and allowed to relax. Consequently, these samples generally had less percent latency. However, conclusions regarding the overall effect of quenching was hard to determine from the above data.

The results of the MORTHANE® PS 370-200 samples at 90° C. indicate that stretch holding and cooling rate has a more significant effect on the percent latency than similar samples tested at 70° C. In these samples, slow cooling produced the best results in percent latency.

Example 5

Effect of Type of Microwave Generator on the Percent Recovery of Locked-in Shape Deformation Rectangular strips of MORTHANE® PS 370-200 were stretched using a fast stretch rate and a draw ratio of 6x. The strips were stretched using a Sintech tensile tester (SINTECH 1/D) and an environmental chamber. The strips were then exposed to microwaves from diffuse a microwave oven or an industrial microwave unit. Both microwave generators operated at 2450 MHz and approximately 900 W. The diffuse microwave unit was a standard household microwave oven manufactured by General Electric.

The results of the tests are given below in Table 5.

TABLE 5

Type of Microwave Oven Results

| Type of Oven | Diffuse | Industrial |
|---|---|---|
| % Recovery | Up to 45% | 60% |

As can be seen in Table 5, the type of microwave oven effects the percent recovery of MORTHANE® PS 370-200. In the diffuse household microwave oven, the multi-mode microwaves are distributed throughout the cavity; however, in the industrial microwave oven, the single-mode resonating cavity is providing more efficient delivery and absorption of EMR by EMR responsive material.

Example 6

Determining Optimum Power and Speed of Industrial Microwave Generator to Maximize the Percent Recovery of Locked-in Shape Deformation Rectangular strips of MORTHANE® PS 370-200 were stretched using a fast stretch rate and a draw ratio of 6x. The strips were stretched using a Sintech tensile tester (SINTECH 1/D) and an environmental chamber. The strips were then exposed to microwaves from the industrial microwave unit described in Example 5. The industrial microwave generator operated at 2450 MHz. The power was adjusted from as low as approximately 220 W. to as much as approximately 900 W. The speed of the sample through the generator was adjusted from as low as about 17.1 ft/min to as much as about 120 ft/min.

The results of the tests are shown in FIG. 4.

Example 7

Activation of Sample Using EMR Energy

Rectangular strips of MORTHANE® PS 370-200 were stretched to 6 times their initial length at 70° C. using a Sintech tensile tester (SINTECH 1/D) and an environmental chamber. The resulting latent (locked in) deformation was 135%. The stretched film was placed on a polypropylene, nonwoven web running at a speed of 68 ft/min.

The web and the film were run through an electromagnetic radiation (EMR) application system operating at 900 W. The EMR application system consisted of a National GEN6KWCONTROLA remote control unit coupled to a Spellman MG10series switch-mode power supply. These units powered a 2450 mHz microwave generator from Richardson Electronics. The microwaves were passed through a directional coupler, waveguide, and stub tuner to a single mode resonating cavity. Forward and reflected power were adjusted and optimized for various materials through adjustments to the generator control and stub tuner.

The time of exposure to microwave irradiation was approximately 0.3 seconds. The measured dimensional change of the film in the machine direction (MD) after EMR treatment was 57% based on the stretched film length.

Comparative Example 1

Activation of Sample Using Thermal Energy

A MORTHANE® PU PS 370-200 film sample was stretched using the procedure of Example 7. The stretched sample was placed in a convection oven for 20 minutes at a temperature of 73° C. The sample was removed from the oven, and its dimensions were measured. The dimensional change of the film in the MD after thermal treatment was 25% based on the stretched film length.

Example 8

Activation of Sample Using EMR Energy

Rectangular strips of MORTHANE® PU PS 370-200 were stretched to 6 times their original length at 90° C. using a Sintech tensile tester (SINTECH 1/D) and an environmental chamber. The resulting latent deformation was 220%. The stretched film was placed on a polypropylene nonwoven web running at a speed of 68 ft/min.

The web and the film were run through an EMR application system as in Example 7 operating at 880 W. The time of exposure to microwave irradiation was approximately 0.3 seconds. The measured dimensional change of the film in MD after EMR treatment was 67% based on the stretched film length.

Comparative Example 2

Activation of Sample Using Thermal Energy

A MORTHANE® PU PS 370-200 film sample was stretched using the same procedure as in Example 8. The measured latent deformation was 165%. The stretched sample was placed in a convection oven and held for 20 minutes at a temperature of 90° C. The sample was removed, and its dimensions were measured. The dimensional change of the film in the MD was 47% based on the stretched film length.

Example 9

Activation of Sample Using EMR Energy

Rectangular strips of MORTHANE® polyester based PU PS 79-200 were stretched to 6 times their original length at 25° C. using a Sintech tensile tester. The resulting latent deformation was 120%. The stretched film was placed on a polypropylene nonwoven web running at a speed of 140 ft/min.

The web and the film were run through the EMR application system of Example 7 operating at 860 W. The time of exposure to microwave irradiation was approximately 0.1 seconds. The measured dimensional change of the film in MD after EMR treatment was 46% based on the stretched film length.

Example 10

Activation of Sample Using EMR Energy

A 90/10 blend of MORTHANE® PU PS 370-200 and polyethylene oxide (PEO) was produced using a Haake laboratory twin screw extruder. Rectangular strips of film made from the 90/10 blend of PU PS 370-200 and PEO were stretched to 6 times their original length at 50° C. using a Sintech tensile tester and an environmental chamber. The resulting latent deformation was 180%. The stretched film was placed on a polypropylene nonwoven web running at a speed of 140 ft/min.

The web and the film were run through the EMR application system of Example 7 operating at 1250 W. The time of exposure to microwave radiation was approximately 0.1 seconds. The measured dimensional change of the film in the MD after EMR treatment was 45% based on a stretched film length.

Example 11

Activation of Sample Using EMR Energy

A multi-layer film of eight alternating layers of MORTHANE® PU PS 370-200 and PEO resin was produced using a microlayer coextrusion line available at Case Western Reserve University (Cleveland, Ohio). The PEO resin POLYOX® WSR-N-3000 was supplied by Union Carbide Corporation in powder form and pelletized at Planet Polymer Technologies (San Diego, Calif.). Rectangular strips of the multi-layer PU PS 370-200/PEO (50/50) film were stretched to 5 times their original length at 25° C. using a Sintech tensile tester. The resulting latent deformation was 270%. The resulting film samples were placed on a polypropylene nonwoven web running at a speed of 68 ft/min.

The web and the film were run through the EMR application system of Example 7 operating at 900 W. The time of exposure to microwave radiation was approximately 0.3 seconds. The measured dimensional change of the film in the MD after EMR treatment was 54% based on the stretched film length.

Comparative Example 3

Activation of Sample Using Thermal Energy

The multi-layer PU PS 370-200/PEO (50/50) film of Example 11 was stretched to 6 times its original length at 25° C. using a Sintech tensile tester. The resulting latent deformation was about 330%. The stretched sample was placed in a convection oven for 20 minutes at a temperature of 73° C. The sample was removed from the oven, and its dimensions were measured. The dimensional change of the film in the MD was 65% based on the stretched film length.

Comparative Example 4

Activation of Sample Using Thermal Energy

A 50/50 blend of PU PS 370-200 and polyethylene oxide (PEO) was produced using a Haake laboratory twin screw extruder. Rectangular strips of film, made from the 50/50 blend, were stretched to 6 times their original length at 25° C. The resulting latent deformation was about 170%. The stretched sample was placed in a convection oven for 20 minutes at a temperature of 65° C. The sample was removed from the oven, and its dimensions were measured. The dimensional change of the film in the MD was 63% based on the stretched film length.

Examples 10, 11 and Comparative Examples 3 and 4 demonstrate that blending or multi-layering/micro-layering of a shape deformation elastomer with another non-elastomeric shape deformation polymer can improve latent deformation properties, especially at lower stretching temperatures, and can significantly increase recoverable deformation as a result of activation by thermal energy or EMR energy.

Example 12

Effect of Activation Energy on the Temperature of a Shape Deformable Material

Rectangular strips of MORTHANE® PS 370-200 were stretched using a slow stretch rate or a fast stretch rate. The strips were stretched at a draw ratio of 6 times their initial length at a temperatures of 80° C. using a Sintech tensile tester (SINTECH 1/D) and an environmental chamber.

The strips were exposed to microwave radiation from an industrial microwave application system, which generated microwaves at 2450 MHz at a power level of 1.5 kW with a reflected power of 1.0 kW. The speed of the film samples through the microwave application system was about 59 ft/min., providing an exposure time of about 0.3 seconds. The system was described in Example 7 in further detail.

The average measured dimensional change of the film samples in the machine direction after EMR treatment was about 50% based on the stretched film length. The average temperature across the surface of the film samples was after EMR treatment was about 36.7° C. as measured by the above-described procedure.

Comparative Example 5

Effect of Thermal Energy on the Temperature of a Shape Deformable Material

Rectangular strips of MORTHANE® PS 370-200 were stretched as in Example 12. The strips were exposed to thermal energy from a hot air oven. The film samples were placed in the convection oven at 37° C.

Two sets of film samples were placed in the oven. One set of film samples were placed in the oven for 15 seconds, while the second set of film samples were placed in the oven for 15 minutes. The first set of film samples exhibited no substantial change in the machine direction after exposure for 15 seconds. The second set of film samples exhibited a change in the machine direction of about 20% after exposure for 15 minutes.

The average measured dimensional change of the film samples in the machine direction after EMR treatment was about 50% based on the stretched film length. The average temperature across the surface of the film samples was after EMR treatment was about 36.7° C. as measured by the above-described procedure.

Comparative Example 6

Effect of Thermal Energy at a Higher Temperature on the Temperature of a Shape Deformable Material Rectangular strips of MORTHANE® PS 370-200 were stretched and thermally heated as in Comparative Example 5 except that the oven temperature was set at 50° C.

The first set of film samples exhibited a change in the machine direction of about 17% after exposure for 15 seconds. The second set of film samples exhibited a change in the machine direction of about 30% after exposure for 15 minutes.

The average measured dimensional change of the film samples in the machine direction after EMR treatment was about 50% based on the stretched film length. The average temperature across the surface of the film samples was after EMR treatment was about 36.7° C. as measured by the above-described procedure.

As shown in Example 12 and Comparative Examples 5 and 6, exposure to microwave radiation produced greater changes in the machine direction of a stretched film than exposure to thermal energy, even though the time of exposure was significantly less. Further, microwave exposure did not result in a substantial change in the temperature of the film samples, as opposed to the changes observed in a convection oven.

Example 13

Non-elastomeric shape deformable material

Rectangular strips of poly (butylenes succinate adipate) copolymer, aliphatic polyester BIONOLLE® 3001 thermoplastic resin obtained from Showa Highpolymer Co. Ltd. (Japan), were stretched at 65° C. using a tensile tester and environmental chamber up to 5× of stretch ratio in the machine direction (MD). The percent latent deformation was measured to be about 280% based on the initial length of the film.

The stretched strips of BIONOLLE® 3001 were placed in a convection oven for 20 minutes at a temperature of 750° C. After 20 minutes, the sample was removed from the oven, and its dimensions were measured. The dimensional change (shrinkage) of the film in the MD after thermal treatment was 35% based on the stretched film length.

The stretched strips of BIONOLLE® 3001 with latent deformation of about 280% in MD were exposed to EMR for about 45 seconds using a standard household microwave oven manufactured by GE and operating at 2450 MHz and approximately 900 W. After 45 seconds, the sample was removed from the microwave oven, and its dimensions were measured. The dimensional change (shrinkage) of the film in the MD after thermal treatment was 25% based on the stretched film length.

The dielectric properties of the BIONOLLE® 3001 film samples were measured at a temperature of 25° C. and a frequency of 2450 MHz. The dielectric constant, e', was 1.55 and the dielectric loss factor, e", was 0.0502. The high dielectric loss factor indicates that the BIONOLLE® 3001 comprises groups with large dipole moments and can be responsive to EMR.

These examples demonstrate that non-elastomeric polymer can possess a shape deformation property, which can be activated by heat. Also, this shape deformation can be activated by using EMR, when the non-elastomeric shape deformation material comprises groups such as, e.g., ester groups, having large dipole moments and providing sufficiently large dielectric loss factor.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of preparing an EMR responsive material having an amount of locked-in shape deformation, wherein the process comprises:

stretching the EMR responsive material to impart a latent deformation in the material.

2. The method of claim 1, wherein the stretched material possesses a draw or stretch ratio of at least 1.5 in one or more directions.

3. The method of claim 2, wherein the stretched material possesses a draw or stretch ratio in one or more directions of from about 2 to about 10.

4. The method of claim 3, wherein the stretched material possesses a draw or stretch ratio in one or more directions of from about 3 to about 7.

5. The method of claim 1, wherein the EMR responsive material is heated during stretching to a temperature of not more than about 120° C.

6. The method of claim 5, wherein the EMR responsive material is heated during stretching to a temperature of not more than about 90° C.

7. The method of claim 1, wherein the stretching is accomplished at a rate of between about 50%/min. to about 5000%/min.

8. The method of claim 7, wherein the stretching is accomplished at a rate of between about 100%/min. to about 2500%/min.

9. The method of claim 1, wherein the EMR responsive material comprises at least one shape deformable matrix material;

wherein the EMR responsive material is capable of being deformed in at least one spatial dimension when exposed to one or more external forces, is capable of maintaining a degree of deformation in at least one spatial dimension once the external force is removed, and is capable of exhibiting a change, or percent recovery, in at least one spatial dimension when subjected to an activation energy in the form of electromagnetic radiation for less than about one second.

10. The method of claim 9, further comprising an electromagnetic absorber.

11. The method of claim 10, further comprising a non-activatable additional material.

12. The method of claim 1, further comprising the step of treating the material to enhance the latent deformation.

13. The method of claim 12, wherein the step of treating the material to enhance the latent deformation is selected from UV treatment, ultrasonic treatment, high energy treatment, or combinations of these treatments.

14. The method of claim 1, further comprising the step of activating the EMR responsive material by exposing the EMR responsive material to electromagnetic radiation having a frequency range of about 20 MHz to about 2500 MHz for less than about one second.

15. The method of claim 14, wherein the EMR responsive material exhibits a temperature change of less than about 15° C. when subjected to the electromagnetic radiation.

16. The method of claim 15, wherein the EMR responsive material exhibits a temperature change of less than about 10° C. when subjected to the electromagnetic radiation.

17. The method of claim 16, wherein the EMR responsive material exhibits a temperature change of less than about 8° C. when subjected to the electromagnetic radiation.

18. The method of claim 17, wherein the EMR responsive material exhibits a temperature change of less than about 5° C. when subjected to the electromagnetic radiation.

19. The method of claim 1, wherein the shape deformable polymer has a dielectric loss factor at a given frequency within the EMR frequency range of from about 10 MHz to about 30 GHz of greater than about 0.05.

20. The method of claim 19, wherein the shape deformable polymer has a dielectric loss factor at a given frequency within the EMR frequency range of from about 10 MHz to about 30 GHz of greater than about 0.1.

21. The method of claim 20, wherein the shape deformable polymer has a dielectric loss factor at a given frequency within the EMR frequency range of from about 10 MHz to about 30 GHz of greater than about 0.20.

22. The method of claim 21, wherein the shape deformable polymer has a dielectric loss factor at a given frequency within the EMR frequency range of from about 10 MHz to about 30 GHz of greater than about 0.25.

* * * * *